US010584268B2

(12) United States Patent
Kasemi et al.

(10) Patent No.: US 10,584,268 B2
(45) Date of Patent: Mar. 10, 2020

(54) COLD CURING EPOXY RESIN PRIMER OR ADHESIVE

(71) Applicant: SIKA TECHNOLOGY AG, Baar (CH)

(72) Inventors: Edis Kasemi, Zürich (CH); Andreas Kramer, Zürich (CH); Ursula Stadelmann, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 17 days.

(21) Appl. No.: 15/559,274

(22) PCT Filed: Mar. 23, 2016

(86) PCT No.: PCT/EP2016/056362
§ 371 (c)(1),
(2) Date: Sep. 18, 2017

(87) PCT Pub. No.: WO2016/151007
PCT Pub. Date: Sep. 29, 2016

(65) Prior Publication Data
US 2018/0094175 A1 Apr. 5, 2018

(30) Foreign Application Priority Data
Mar. 23, 2015 (EP) .................... 15160411

(51) Int. Cl.
| *C09J 163/00* | (2006.01) |
| *C08G 59/24* | (2006.01) |
| *C08G 59/36* | (2006.01) |
| *C08G 59/50* | (2006.01) |
| *C08G 59/40* | (2006.01) |
| *C08L 63/00* | (2006.01) |
| *C07C 215/50* | (2006.01) |
| *C09D 7/63* | (2018.01) |
| *C08G 59/64* | (2006.01) |
| *C09D 163/00* | (2006.01) |
| *B32B 27/38* | (2006.01) |
| *C08K 5/07* | (2006.01) |
| *C08K 5/17* | (2006.01) |

(52) U.S. Cl.
CPC ............ *C09J 163/00* (2013.01); *B32B 27/38* (2013.01); *C07C 215/50* (2013.01); *C08G 59/245* (2013.01); *C08G 59/36* (2013.01); *C08G 59/4007* (2013.01); *C08G 59/5026* (2013.01); *C08G 59/5033* (2013.01); *C08G 59/64* (2013.01); *C08K 5/07* (2013.01); *C08K 5/17* (2013.01); *C08L 63/00* (2013.01); *C09D 7/63* (2018.01); *C09D 163/00* (2013.01); *C07C 2601/14* (2017.05)

(58) Field of Classification Search
None
See application file for complete search history.

(56) References Cited

U.S. PATENT DOCUMENTS

| 3,217,039 | A | 11/1965 | Humber | |
| 4,399,268 | A * | 8/1983 | Becker | C03C 17/38 |
| | | | | 525/490 |
| 2014/0128506 | A1 | 5/2014 | Kramer et al. | |
| 2014/0357763 | A1* | 12/2014 | Balijepalli | C08G 59/50 |
| | | | | 523/428 |
| 2016/0060383 | A1* | 3/2016 | Shen | C08G 59/02 |
| | | | | 523/400 |

FOREIGN PATENT DOCUMENTS

| CN | 102061061 A | 5/2011 | | |
| EP | 2546276 A1 | 1/2013 | | |
| JP | 2004-299238 A | 10/2004 | | |
| JP | 2004299238 A * | 10/2004 | | |
| RU | 2146245 C1 | 3/2000 | | |
| WO | WO-2013101740 A2 * | 7/2013 | ............. | C08G 59/50 |
| WO | WO-2014179975 A1 * | 11/2014 | ............. | C08G 59/02 |

OTHER PUBLICATIONS

English machine translation of JP2004-299238A prepared Mar. 17, 2019. (Year: 2019).*
Jun. 2, 2016 International Search Report issued in International Patent Application No. PCT/EP2016/056362.
Harada, Yasuhiro et al: "Polyolefin-lined steel article with high interlayer adhesion and corrosion resistance", Chemical Abstracts Service, XP002757975, May 24, 2016.
Zhang, Wenquan et al: "Method for preparing exfoliation-type montmorillonite/epoxy resin composite", Chemical Abstracts Service, XP002757976, May 24, 2016.
Chemical Abstracts Service, XP002757977, Oct. 8, 1999, Database accession No. 244020-66-4.
Chemical Abstracts Service, XP002757978, Nov. 7, 2008, Database accession No. 1071587-03-5.
Sep. 26, 2017 International Preliminary Report on Patentability issued in International Patent Application No. PCT/EP2016/056362.
Jan. 21, 2019 Office Action issued in European Patent Application No. 16714323.9.
Sep. 20, 2019 Office Action issued in Russian Patent Application No. 2017132420/04(057061).

* cited by examiner

*Primary Examiner* — Christopher M Rodd
(74) *Attorney, Agent, or Firm* — Oliff PLC

(57) ABSTRACT

The invention relates to the use of an epoxy resin composition, containing at least one reaction product from the reaction of at least one amine of formula (I) with at least one carbonyl compound of formula (II) and hydrogen, as a cold curing primer or adhesive. Primers or adhesives of this type cure rapidly and trouble-free at ambient temperature, even at cold temperatures such as 10 or 5° C., suffer remarkably little yellowing and are free from toxic phenol compounds such as phenol, tert-butylphenol or nonylphenol. The primer has a particularly low viscosity and is particularly suitable for priming porous mineral substrates.

14 Claims, No Drawings

COLD CURING EPOXY RESIN PRIMER OR ADHESIVE

TECHNICAL FIELD

The invention pertains to the field of hardeners for epoxy resins, epoxy resin compositions, and the use thereof as primer or adhesive.

PRIOR ART

Primers based on epoxy resins are often used as undercoat or primer in coatings with multicoat constructions, especially in exterior applications, as for example in floor coverings, multistorey carpark coatings, bridge seals, balcony coatings or anticorrosion coatings. The primer in this case is to have a low viscosity, so that it flows readily, effectively wets the base or the substrate and penetrates it to a certain degree, in order to close pores and cracks and so to consolidate the substrate. At ambient temperature, moreover, the primer is to have a sufficiently long pot life to allow it to be easily worked by hand, and is then to cure rapidly, even in cold conditions, so that the area treated with the primer can be worked on further soon after. After curing has taken place, the primer is to form a firm, non-tacky film which develops effective adhesion to the substrate and, when coated over, effective adhesion to the topcoat, hence serving as a tie between substrate and topcoat. In the case of porous mineral substrates, especially cementitious substrates such as concrete or mortar, the primer serves in particular for the closing of the pores and hence as a barrier toward moisture from below, and also for the binding of dust.

In order to achieve these properties, hardeners used for primers in the prior art are often what are called Mannich bases, which represent reaction products of phenols, formaldehyde and amines. Mannich bases allow the required high cure rates, not least at cool ambient temperatures in the range from 5 to 15° C., and are not susceptible to the curing defects which are known as "blushing" and are caused by formation of salts with $CO_2$ from the air. On the basis of their preparation, they include a considerable portion of free toxic phenols, such as phenol, tert-butylphenol or nonylphenol, for example. Phenols of this kind are poisonous to people and the environment (reproductive toxicity, water-body toxicity) and therefore necessitate precautionary and protective measures during processing, storage and transport. They are not incorporated chemically into the polymer in the course of curing, and for that reason they may escape into the environment by outgassing or leaching, and may therefore also pose a risk over the long term. Phenol-free substitutes known to date for hardeners based on Mannich bases all have weaknesses in the technical performance capacity, and alternatively have too high a viscosity, hence necessitating heavy dilution with unwanted VOC solvents, an excessive sensitivity to blushing, excessively slow curing, particularly under cold conditions, or a curing outcome comprising soft polymers with little mechanical load-bearing capacity.

U.S. Pat. No. 4,399,268 describes reaction products containing phenol groups from the monoalkylation of m-xylylenediamine, including reaction products from the reductive alkylation with hydroxyaldehydes, which are suitable as hardeners for coatings of high chemical resistance, which can be used in coatings with food contact, as for example in preserve cans. The process described produces high-viscosity reaction products and compositions. Use as a primer is not described.

U.S. Pat. No. 8,729,213 describes benzylated polyamine hardeners and the use thereof in epoxy resins. Reaction products primarily described are products from the reductive alkylation of meta-xylylenediamine with benzaldehyde in various proportions. Reaction products of this kind, although of very low viscosity, generally have an insufficient reaction rate under cold conditions when used as hardeners for primers. Also mentioned is the possibility of using, rather than benzaldehyde, reaction products originating from vanillin (4-hydroxy-2-methoxybenzaldehyde). Such reaction products, however, have a very high viscosity and are therefore not very advantageous for primers.

SUMMARY OF THE INVENTION

It is an object of the invention to provide an epoxy resin composition for use as a primer which cures rapidly at ambient temperature, including in particular under cold conditions, is of sufficiently low viscosity for use on porous mineral substrates, and is largely free of toxic phenol compounds such as phenol, tert-butylphenol or nonylphenol.

Surprisingly this object is achieved with an epoxy resin composition as described in claim 1. The reaction product contained in the composition is preparable in a simple operation from readily available starting materials and contains no free phenols such as phenol, tert-butylphenol or nonylphenol. On account of the high diluent effect of the reaction product, the composition is of surprisingly low viscosity, even without low molecular weight constituents such as free phenols or solvents. The curing of the composition has a similar rapidity to that of compositions based on conventional Mannich bases, including in particular at cold ambient temperatures below 20° C. or below 10° C.

The rapid curing is surprising because the phenolic group of the reaction product is incorporated chemically, on curing, into the resulting epoxide polymer, and the assumption would be that this would cause its accelerating effect to fall. The attainable time to a tack-free state is much shorter and the ultimate strength is much higher than when using comparable reaction products prepared starting from similar amines.

The low viscosity and good diluent effect of the reaction product are likewise surprising. Corresponding reaction products, derived from carbonyl compounds which are analogous to the carbonyl compounds of the formula (II) but in which the phenolic OH group is located in meta position or para position to the carbonyl substituents have a viscosity which is higher by a multiple factor.

The epoxy resin composition of claim 1 is therefore outstandingly suitable as a primer, especially for use on porous mineral substrates and also under cold ambient conditions, of the kind typical on building sites. The low viscosity allows effective wetting and depth of penetration into the porous substrate, with the pores being filled and closed. The rapid curing allows the primer to accept foot traffic soon after application and/or to be topcoatable soon after application.

The epoxy resin composition is suitable, moreover, as an adhesive, especially for use at cold temperatures, as for example outdoors on building sites or in unheated industrial halls. On the basis of the rapid curing, an adhesive bond is load-bearing after a short time even in cold temperatures, thus allowing rapid progress of building and short cycle times. The low viscosity means that the adhesive can be filled to a high degree with, for example, finely ground quartz or silica sand, this being an advantage, for example, for use as an adhesive mortar.

The ultimate strength and resistance of the composition are very high and satisfy extremely exacting requirements. The composition, moreover, is virtually colorless and exhibits an extremely low propensity to yellow under the influence of light, in spite of the high aromatic fraction in the reaction product contained therein. This permits a high level of design freedom in the context of use as a primer or adhesive, meaning, for example, that a visible adhesive joint need not be painted over; a primer in a coating system can be given a thin overcoating or an overcoating with a low degree of pigmentation, or may remain entirely without overcoating in the edge region of adhesive joints or coatings, without any esthetic detriment or visible color change.

Further aspects of the invention are subjects of further independent claims. Particularly preferred embodiments of the invention are subjects of the dependent claims.

CERTAIN EMBODIMENTS OF THE INVENTION

A subject of the invention is the use of an epoxy resin composition comprising at least one reaction product from the reaction of at least one amine of the formula (I) with at least one carbonyl compound of the formula (II) and hydrogen, $$NH_2-CH_2-A-CH_2-NH_2 \quad (I)$$

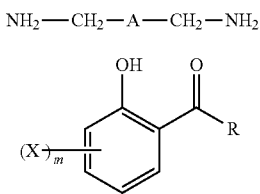

(II)

where
A is a phenylene radical or cyclohexylene radical,
R is a hydrogen radical or alkyl radical having 1 to 8 carbon atoms,
m is 0 or 1, and
X is a hydroxyl radical or methyl radical or methoxy radical,
where the molar ratio between the amine of the formula (I) and the carbonyl compound of the formula (II) is in the range from 1/0.7 to 1/1.2,
as a cold-curing primer or adhesive.

A "primer" is a curable composition which is used as a priming coat or undercoat by being applied two-dimensionally to a substrate or base and thereafter covered with a further layer. On curing, the primer forms a film which prepares the substrate or base for the subsequent layer and serves as a tie. The film thickness of the applied primer is typically on average below 0.5 mm.

"Cold-curing" refers to a primer or adhesive which can be worked and cured at ambient temperature, more particularly in the range from 5 to 35° C. Substance names beginning with "poly", such as polyamine, polyol or polyepoxide, refer to substances which viewed formally contain two or more per molecule of the functional groups that occur in their name.

A "primary amino group" is an amino group which is bonded to a single organic radical and carries two hydrogen atoms; a "secondary amino group" is an amino group which is bonded to two organic radicals, which may also together be part of a ring, and carries one hydrogen atom; and a "tertiary amino group" is an amino group which is bonded to three organic radicals, which may also, as a pair or as a trio, be part of one or more rings, and carries no hydrogen atom.

"Amine hydrogen" refers to the hydrogen atoms of primary and secondary amino groups.

"Amine hydrogen equivalent weight" refers to the mass of an amine or amine-containing composition which contains one mole equivalent of amine hydrogen.

A "diluent" is a substance which is soluble in an epoxy resin and lowers the viscosity of the resin, and is not incorporated chemically into the epoxide polymer in the course of curing.

"Viscosity" refers to the dynamic viscosity or shear viscosity, which is defined by the ratio between the shear stress and the shear rate (rate gradient) and is determined as described in the description and in the working examples.

"Room temperature" refers to a temperature of 23° C.

The epoxy resin composition is preferably applied and cured at ambient temperature, preferably at a temperature in the range from 5 to 35° C., more preferably 10 to 30° C. This is especially advantageous for outdoor applications, on building sites and in unheated industrial halls.

The radical A is preferably substituted in 1,3- or in 1,4-position. A is therefore preferably 1,3-phenylene, 1,4-phenylene, 1,3-cyclohexylene or 1,4-cyclohexylene. These amines of the formula (I) are particularly easily accessible and particularly reactive.

More preferably A is 1,3-phenylene or 1,3-cyclohexylene. These amines of the formula (I) permit reaction products of particularly low viscosity.

The amine of the formula (I) is preferably selected from the group consisting of 1,3-bis(aminomethyl)benzene and 1,3-bis(aminomethyl)cyclohexane.

Preferably R is a hydrogen radical or an alkyl radical having 1 to 4 carbon atoms, more particularly methyl, ethyl or isopropyl.

More preferably R is a hydrogen radical or is a methyl radical.

Most preferably R is a hydrogen radical.

Preferably m is 0. These carbonyl compounds of the formula (II) allow reaction products of particularly low viscosity.

Preferred carbonyl compounds of the formula (II) are 2-hydroxybenzaldehyde (salicylaldehyde), 2-hydroxy-3-methylbenzaldehyde, 2-hydroxy-5-methyl benzaldehyde, 2-hydroxy-3-m ethoxybenzaldehyde, 2-hydroxy-4-methoxybenzaldehyde, 2-hydroxy-5-methoxybenzaldehyde, 2'-hydroxyacetophenone and 2-hydroxy-4-m ethoxybenzophenone. These carbonyl compounds are either liquid at room temperature or low-melting with a melting point below 60° C., thus permitting easy handling.

With particular preference the carbonyl compounds of the formula (II) is selected from the group consisting of salicylaldehyde and 2'-hydroxyacetophenone. These carbonyl compounds are easily obtainable, liquid at room temperature, and permit reaction products which are of particularly low viscosity and are particularly easy to prepare.

The most preferred is salicylaldehyde. With this compound, reaction products are obtained that are especially of low viscosity and reactive.

The molar ratio between the amine of the formula (I) and the carbonyl compound of the formula (II) is preferably in the range from 1/0.8 to 1/1.1, more particularly 1/0.9 to 1/1. At this molar ratio, the resultant reaction products are particularly reactive with a particularly good diluent effect.

The reaction of at least one amine of the formula (I) with at least one carbonyl compound of the formula (II) and hydrogen is also referred to as reductive alkylation. It may take place directly with molecular hydrogen or indirectly by hydrogen transfer from other reagents. Preference is given to using molecular hydrogen. The reaction conditions are selected advantageously such that the amine of the formula (I) is to a large extent only monoalkylated, and the aromatic ring of the carbonyl compound of the formula (II) is not hydrogenated. Preference is given to working under a hydrogen pressure of 5 to 100 bar, at a temperature of 40 to 120° C., more particularly 60 to 100° C., and in the presence of a suitable catalyst. Preferred as catalyst are palladium on carbon (Pd/C), platinum on carbon (Pt/C), Adams catalyst or Raney nickel, more particularly palladium on carbon.

The reaction may be carried out solventlessly or, preferably, in a solvent, such as ethanol or isopropanol, for example. Any solvent present is preferably removed after the reaction, more particularly by means of distillation.

The reaction product from this reaction typically contains an amount of amine of the formula (III) in the range from 30 to 80 weight %.

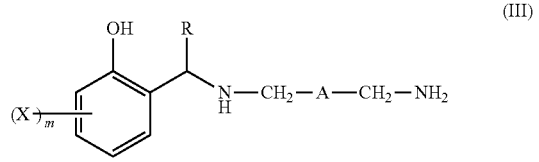

(III)

In the formula (III) A, R, m and X have the definitions already stated.

The further constituents of the reaction product consist primarily of amine of the formula (I) and polyalkylated products, more particularly N,N'-dialkylation products of the formula

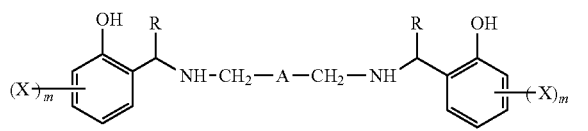

The epoxy resin composition preferably comprises
a resin component comprising at least one epoxy resin and
a hardener component comprising the reaction product from the reaction of at least one amine of the formula (I) with at least one carbonyl compound of the formula (II) and hydrogen, as described above.

The resin component and the hardener component are typically present in separate containers and are each storage-stable per se. They are not mixed with one another until immediately prior to application, when their reactive groups come into contact with one another and the composition cures.

Suitability as epoxy resin is possessed by customary technical epoxy resins. These are obtained in a known manner, as for example from the oxidation of the corresponding olefins or from the reaction of epichlorohydrin with the corresponding polyols, polyphenols or amines.

Particularly suitable as epoxy resin are what are called liquid resins. These have a glass transition temperature below 25° C.

Likewise possible as epoxy resin are what are called solid resins, which have a glass transition temperature above 25° C. and can be comminuted to powders which are pourable at 25° C.

Suitable epoxy resins are, in particular, aromatic epoxy resins, more particularly the glycidylization products of:
bisphenol A, bisphenol F or bisphenol A/F, where A stands for acetone and F for formaldehyde, which served as reactants in the preparation of these bisphenols. In the case of bisphenol F, there may also be positional isomers present, derived more particularly from 2,4'- or 2,2'-hydroxyphenylmethane;
dihydroxybenzene derivatives such as resorcinol, hydroquinone or pyrocatechol;
further bisphenols or polyphenols such as bis(4-hydroxy-3-methylphenyl)methane, 2,2-bis(4-hydroxy-3-methylphenyl)propane (bisphenol C), bis(3,5-dimethyl-4-hydroxyphenyl)methane, 2,2-bis(3,5-dimethyl-4-hydroxyphenyl)propane, 2,2-bis(3,5-dibromo-4-hydroxy-phenyl)propane, 2,2-bis(4-hydroxy-3-tert-butylphenyl)propane, 2,2-bis(4-hydroxyphenyl)butane (bisphenol B), 3,3-bis(4-hydroxyphenyl)pentane, 3,4-bis(4-hydroxyphenyl)hexane, 4,4-bis(4-hydroxyphenyl)heptane, 2,4-bis(4-hydroxyphenyl)-2-methylbutane, 2,4-bis(3,5-dimethyl-4-hydroxyphenyl)-2-methylbutane, 1,1-bis(4-hydroxyphenyl)cyclohexane (bisphenol Z), 1,1-bis(4-hydroxyphenyl)-3,3,5-trimethylcyclohexane (bisphenol-TMC), 1,1-bis(4-hydroxyphenyl)-1-phenylethane, 1,4-bis[2-(4-hydroxyphenyl)-2-propyl]benzene (bisphenol P), 1,3-bis[2-(4-hydroxyphenyl)-2-propyl]benzene (bisphenol M), 4,4'-dihydroxybiphenyl (DOD), 4,4'-dihydroxybenzophenone, bis(2-hydroxynaphth-1-yl)methane, bis(4-hydroxynaphth-1-yl)methane, 1,5-dihydroxynaphthalene, tris(4-hydroxyphenyl)methane, 1,1,2,2-tetrakis(4-hydroxyphenyl)ethane, bis(4-hydroxyphenyl) ether or bis(4-hydroxyphenyl) sulfone;
condensation products of phenols with formaldehyde which are obtained under acidic conditions, such as phenol novolaks or cresol novolaks;
aromatic amines, such as aniline, toluidine, 4-aminophenol, 4,4'-methylenediphenyldiamine, 4,4'-methylenediphenyldi-(N-methyl)amine, 4,4'-[1,4-phenylenebis(1-methylethylidene)]bisaniline (bisaniline P) or 4,4'-[1,3-phenylenebis(1-methylethylidene)]bisaniline (bisaniline M).

Further suitable epoxy resins are aliphatic or cycloaliphatic polyepoxides, more particularly
glycidyl ethers of saturated or unsaturated, branched or unbranched, cyclic or open-chain di-, tri- or tetrafunctional $C_2$ to $C_{30}$ alcohols, especially ethylene glycol, propylene glycol, butylene glycol, hexanediol, octanediol, polypropylene glycols, dimethylolcyclohexane, neopentyl glycol, dibromoneopentyl glycol, castor oil, trimethylolpropane, trimethylolethane, pentaerythritol, sorbitol or glycerol, or alkoxylated glycerol or alkoxylated trimethylolpropane;
a hydrogenated bisphenol A, F or A/F liquid resin, or the glycidylization products of hydrogenated bisphenol A, F or A/F;
an N-glycidyl derivative of amides or heterocyclic nitrogen bases, such as triglycidyl cyanurate or triglycidyl isocyanurate, or reaction products of epichlorohydrin with hydantoin;
epoxy resins from the oxidation of olefins, such as, in particular, vinylcyclo-hexene, dicyclopentadiene, cyclohexadiene, cyclododecadiene, cyclododecatriene, isoprene, 1,5-hexadiene, butadiene, polybutadiene or divinylbenzene.

A preferred epoxy resin in the resin component is a liquid resin based on a bisphenol, more particularly a diglycidyl ether of bisphenol A, bisphenol F or bisphenol A/F, of the kind available commercially, for example, from Dow, Huntsman or Momentive. These liquid resins have a low viscosity for epoxy resins and in the cured state exhibit good properties as a coating. They may include fractions of solid bisphenol A resin or phenol novolaks.

The resin component may comprise a reactive diluent, more particularly a reactive diluent having at least one epoxide group. Particularly suitable as reactive diluents are the glycidyl ethers of mono- or polyhydric phenols or aliphatic or cycloaliphatic alcohols, such as, in particular, the aforementioned polyglycidyl ethers of di- or polyols, or, furthermore, phenyl glycidyl ether, cresyl glycidyl ether, guaiacol glycidyl ether, 4-methoxyphenyl glycidyl ether, p-n-butylphenyl glycidyl ether, p-tert-butylphenyl glycidyl ether, 4-nonylphenyl glycidyl ether, 4-dodecylphenyl glycidyl ether, cardanol glycidyl ether, bertyl glycidyl ether, allyl glycidyl ether, butyl glycidyl ether, hexyl glycidyl ether, 2-ethylhexyl glycidyl ether, or glycidyl ethers of natural alcohols such as, in particular, $C_8$ to $C_{10}$ alkyl glycidyl ether or $C_{12}$ to $C_{14}$ alkyl glycidyl ether. The addition of a reactive diluent to the epoxy resin has the effect of reducing the viscosity, and/or of reducing the glass transition temperature and/or the mechanical values.

The epoxy resin composition preferably further comprises at least one diluent and/or at least one accelerator and/or at least one further amine.

This further amine is in particular not an amine of the formula (III) and not a by-product or reactant contained in the reaction product.

Suitability as diluents is possessed more particularly by xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylyl ether, propylene glycol butyl ether, propylene glycol phenyl ether, dipropylene glycol, dipropylene glycol monomethyl ether, dipropylene glycol dimethyl ether, dipropylene glycol di-n-butyl ether, N-methylpyrrolidone, diphenylmethane, diisopropylnaphthalene, petroleum fractions such as, for example, Solvesso® grades (from Exxon), alkylphenols such as tert-butylphenol, nonylphenol, dodecylphenol or cardanol (from cashew shell oil, comprising as principal constituents 3-(pentadeca-8-enyl)phenol, 3-(pentadeca-8,11-dienyl)phenol and 3-(pentadeca-8,11,14-trienyl)phenol), available for example as Cardolite® NC-700 or Cardolite® NX-2026 (both from Cardolite), styrenized phenol, bisphenols, aromatic hydrocarbon resins, especially those containing phenol groups, alkoxylated phenol, especially ethoxylated or propoxylated phenol, more particularly 2-phenoxyethanol, adipates, sebacates, phthalates, benzoates, organic phosphoric acid esters or sulfonic acid esters or sulfonamides. Preferred diluents are benzyl alcohol, styrenized phenol, ethoxylated phenol, or aromatic hydrocarbon resins containing phenol groups, more particularly the Novares® grades LS 500, LX 200, LA 300 or LA 700 (from Rütgers), or Cardanol.

In one preferred embodiment, the epoxy resin composition comprises at least one diluent selected from the group consisting of benzyl alcohol, styrenized phenol, ethoxylated phenol, aromatic hydrocarbon resins containing phenol groups, and cardanol. An epoxy resin composition of this kind is particularly suitable for use as a primer.

It may be advantageous to use a combination of two or more diluents.

Suitable accelerators are substances which accelerate the reaction between amino groups and epoxide groups, more particularly acids or compounds which can be hydrolyzed to acids, more particularly organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecylbenzenesulfonic acid, sulfonic acid esters, other organic or inorganic acids such as, in particular, phosphoric acid, or mixtures of the aforementioned acids and acid esters; tertiary amines such as, in particular, 1,4-diazabicyclo[2.2.2]octane, benzyldimethylamine, α-methylbenzyldimethylamine, triethanolamine, dimethylaminopropylamine, imidazoles such as, in particular, N-methylimidazole, N-vinylimidazole or 1,2-dimethylimidazole, salts of such tertiary amines, quaternary ammonium salts, such as, in particular benzyltrimethylammonium chloride, amidines such as, in particular, 1,8-diazabicyclo[5.4.0]undec-7-ene, guanidines such as, in particular, 1,1,3,3-tetramethylguanidine, phenols, especially bisphenols, phenolic resins, or Mannich bases containing tertiary amino groups, such as, in particular, 2-(dimethylaminomethyl)phenol, 2,4,6-tris(dimethylaminomethyl)phenol or polymers of phenol, formaldehyde and N,N-dimethyl-1,3-propanediamine, phosphites such as, in particular, diphenyl or triphenyl phosphites, or compounds containing mercapto groups. Preferred accelerators are acids, tertiary amines or Mannich bases containing tertiary amino groups.

Most preferred is salicylic acid or 2,4,6-tris(dimethylaminomethyl)phenol or a combination thereof.

Further amines are preferably a constituent of the hardener component. Suitable as further amine are polyamines which have at least two, more particularly at least three, amine hydrogens reactive toward epoxide groups, more particularly the following polyamines:

polyamines having a primary amino group, especially N,N-dimethylamino-propylamine (DMAPA) or N-(3-dimethylaminopropyl)-1,3-propylenediamine (DMAPAPA);

polyamines having one or two secondary amino groups, especially products from the reductive alkylation of primary aliphatic polyamines with aldehydes or ketones not of the formula (III), such as, in particular, N-benzyl-1,2-ethanediamine, N,N'-dibenzyl-1,2-ethanediamine, $N^1$-benzyl-1,2-propanediamine or $N^2$-benzyl-1,2-propanediamine or any desired mixtures of these isomers, N,N'-dibenzyl-1,2-propanediamine, N-benzyl-1,3-bis(aminomethyl)benzene, N,N'-dibenzyl-1,3-bis(aminomethyl)benzene, N-benzyl-1,3-bis(aminomethyl)cyclohexane, N,N'-dibenzyl-1,3-bis(aminomethyl)cyclohexane, N-2-ethylhexyl-1,3-bis(aminomethyl)benzene, N,N'-bis(2-ethylhexyl)-1,3-bis(aminomethyl)benzene, or partially styrenized polyamines such as, in particular, styrenized 1,3-bis(amino-methyl)benzene (available as Gaskamine® 240 from Mitsubishi Gas Chemical);

aliphatic, cycloaliphatic or arylaliphatic primary diamines, especially 2,2-dimethyl-1,3-propanediamine, 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2 (4),4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3- or 1,4-diaminocyclohexane, bis(4-aminocyclohexyl) methane ($H_{12}$-MDA), bis(4-amino-3-methylcyclohexyl)methane, bis(4-amino-3-ethylcyclohexyl)methane, bis(4-amino-3,5-dimethylcyclohexyl)methane, bis (4-amino-3-ethyl-5-methyl-cyclohexyl)methane, 1-amino-3-aminomethyl-3,5,5-trimethylcyclohexane (isophoronediamine or IPDA), 2- or 4-methyl-1,3-diaminocyclohexane or mixtures thereof, 1,3-bis(aminomethyl)cyclohexane, 1,4-bis (aminomethyl)cyclohexane, 2,5(2,6)-bis(aminomethyl)bicyclo[2.2.1] heptane (NBDA), 3(4),8(9)-bis(aminomethyl)tricyclo [$5.2.1.0^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]undecane, 1,3-bis(amino-methyl) benzene (MXDA) or 1,4-bis(aminomethyl)benzene;

aliphatic primary di- or triamines containing ether groups, especially bis(2-aminoethyl) ether, 3,6-dioxaoctane-1, 8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine or higher oligomers of these diamines, bis(3-aminopropyl)polytetrahydrofurans or other polytetrahydrofurandiamines, cycloaliphatic ether group-containing diamines from the propoxylation and subsequent amination of 1,4-dimethylolcyclohexane, obtainable in particular as Jeffamine® RFD-270 (from Huntsman), or polyoxyalkylenedi- or -triamines, which typically represent products from the amination of polyoxyalkylenedi- or -triols and are obtainable, for example, under the name Jeffamine® (from Huntsman), under the name Polyetheramine (from BASF) or under the name PC Amine® (from Nitroil). Especially suitable polyoxyalkylenedi- or -triamines are Jeffamine® D-230, Jeffamine® D-400, Jeffamine® D-2000, Jeffamine® EDR-104, Jeffamine® EDR-148, Jeffamine® EDR-176, Jeffamine® T-403, Jeffamine® T-3000, Jeffamine® T-5000, or corresponding amines from BASF or Nitroil;

polyamines containing secondary amino groups and having two primary aliphatic amino groups, such as, in particular, 3-(2-aminoethyl)aminopropylamine, bis (hexamethylene)triamine (BHMT), diethylenetriamine (DETA), triethylenetetramine (TETA), tetraethylenepentamine (TEPA), pentaethylenehexamine (PEHA) or higher homologs of linear polyethyleneamines such as polyethylenepolyamine having 5 to 7 ethyleneamine units (referred to as "higher ethylenepolyamine", HEPA), products from the multiple cyanoethylation or cyanobutylation and subsequent hydrogenation of primary di- and polyamines having at least two primary amino groups, such as dipropylenetriamine (DPTA), N-(2-aminoethyl)-1,3-propanediamine (N3-amine), N,N'-bis(3-aminopropyl)ethylenediamine (N4-amine), N,N'-bis(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine or N,N'-bis(3-amino-1-ethylpropyl)-2-methyl-1,5-pentane-diamine;

aliphatic, cycloaliphatic or arylaliphatic primary triamines, especially 4-aminomethyl-1,8-octanediamine, 1,3,5-tris(aminomethyl)benzene, 1,3,5-tris-(aminomethyl)cyclohexane, tris(2-aminoethyl)amine, tris(2-amino-propyl)amine or tris(3-aminopropyl)amine;

aromatic polyamines, such as, in particular, m- and p-phenylenediamine, 4,4'-, 2,4' and/or 2,2'-diaminodiphenylmethane, 3,3'-dichloro-4,4'-diamino-diphenylmethane (MOCA), 2,4- and/or 2,6-tolylenediamine, mixtures of 3,5-dimethylthio-2,4- and -2,6-tolylenediamine (available as Ethacure® 300 from Albermarle), mixtures of 3,5-diethyl-2,4- and -2,6-tolylenediamine (DETDA, available as Ethacure® 100 from Albermarle), 3,3',5, 5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4, 4'-diaminodiphenylmethane (M-MIPA), 3,3',5,5'-tetraisopropyl-4,4'-diaminodiphenylmethane (M-DIPA), 4,4'-diaminodiphenyl sulfone (DDS), 4-amino-N-(4-aminophenyl)benzenesulfonamide, 5,5'-methylenedianthranilic acid, dimethyl 5,5'-methylenedianthranilate, 1,3-propylene bis(4-aminobenzoate), 1,4-butylene bis(4-aminobenzoate), polytetramethylene oxide bis(4-aminobenzoate) (available as Versalink® from Air Products), 1,2-bis(2-aminophenylthio)ethane, 2-methylpropyl 4-chloro-3,5-diaminobenzoate or tert-butyl 4-chloro-3,5-diaminobenzoate;

polyamidoamines, especially reaction products of a mono- or polybasic carboxylic acid, and/or the esters or anhydrides thereof, particularly of a dimer fatty acid, with an aliphatic, cycloaliphatic or aromatic polyamine that is used in a stoichiometric excess, more particularly a polyalkyleneamine such as, for example, DETA or TETA, more particularly the commercially available polyamidoamines Versamid® 100, 125, 140 or 150 (from Cognis), Aradur® 223, 250 or 848 (from Huntsman), Euretek® 3607 or 530 (from Huntsman) or Beckopox® EH 651, EH 654, EH 655, EH 661 or EH 663 (from Cytec);

or adducts of polyamines with epoxides or epoxy resins, especially adducts with diepoxides in a molar ratio of approximately 2/1, or adducts with monoepoxides in a molar ratio of approximately 1/1, or reaction products of polyamines and epichlorohydrin, more particularly that of 1,3-bis(amino-methyl)benzene, available commercially as Gaskamine® 328 (from Mitsubishi Gas Chemical).

It may be advantageous if the hardener comprises a combination of two or more further amines.

Preferred as further amine are polyamines having a primary and a secondary amino group, which are not of the formula (III), especially N-benzyl-1,2-ethanediamine, $N^1$-benzyl-1,2-propanediamine or $N^2$-benzyl-1,2-propanediamine or any desired mixtures of these isomers, N-benzyl-1,3-bis(aminomethyl)benzene or N-benzyl-1,3-bis(aminomethyl)cyclohexane. Amines of this kind have a high diluent effect.

Preferred as further amine are also polyamines having a molecular weight of at least 120 g/mol, preferably TMD, $H_{12}$-MDA, IPDA, 2- or 4-methyl-1,3-diaminocyclohexane or mixtures thereof, 1,3-bis(aminomethyl)cyclohexane, 1,4-bis(aminomethyl)cyclohexane, NBDA, MXDA, BHMT, TETA, TEPA, PEHA, DPTA or N4-amine. Amines of this kind have a high diluent effect and a high reactivity, without being excessively volatile.

Additionally preferred as further amine are DMAPA or DMAPAPA. These amines have a high diluent effect and a high reactivity.

Additionally preferred as further amine are adducts, having at least three amine hydrogens, of at least one polyamine having 2 to 12 carbon atoms and at least one epoxide.

Preferred as epoxide for such an adduct are monoepoxides, especially aromatic monoepoxides, more particularly cresyl glycidyl ether, tert-butylphenyl glycidyl ether or the glycidyl ether of cardanol. Particularly preferred is cresyl glycidyl ether. Suitability as cresyl glycidyl ether is possessed by all isomeric cresyl glycidyl ethers or mixtures thereof, especially commercially available products such as, in particular, Araldite® DY-K (from Huntsman), Polypox™ R6 (from Dow), Heloxy™ KR (from Hexion) or Erisys® GE-10 (from CVC Spec. Chem.)

Additionally preferred as an epoxide for such an adduct are diepoxides, especially aromatic diepoxides, more particularly bisphenol A or bisphenol F or bisphenol A/F diglycidyl ether or resorcinol diglycidyl ether, especially liquid resins that are available commercially.

A particularly preferred further amine is $N^1$-benzyl-1,2-propanediamine or $N^2$-benzyl-1,2-propanediamine or any desired mixtures of these isomers. Another particularly preferred further amine is N-benzyl-1,3-bis(amino-methyl)benzene or N-benzyl-1,3-bis(aminomethyl)cyclohexane.

The hardener component may comprise further substances that are reactive toward epoxide groups, examples being monoamines such as hexylamine or benzylamine, or compounds containing mercapto groups, more particularly the following:
liquid, mercaptan-terminated polysulfide polymers, known under the brand name Thiokol® (from Morton Thiokol; available for example from SPI Supplies, or from Toray Fine Chemicals), more particularly types LP-3, LP-33, LP-980, LP-23, LP-55, LP-56, LP-12, LP-31, LP-32 or LP-2; and also known, moreover, under the brand name Thioplast® (from Akzo Nobel), more particularly the types G 10, G 112, G 131, G 1, G 12, G 21, G 22, G 44 or G 4;
mercaptan-terminated polyoxyalkylene ethers, obtainable for example by reaction of polyoxyalkylenediols or -triols either with epichlorohydrin or with an alkylene oxide, followed by sodium hydrogensulfide;
mercaptan-terminated compounds in the form of polyoxyalkylene derivatives known under the brand name Capcure® (from Cognis), especially types WR-8, LOF or 3-800;
polyesters of thiocarboxylic acids, for example pentaerythritol tetramercaptoacetate, trimethylolpropane trimercaptoacetate, glycol dimercaptoacetate, pentaerythritol tetra(3-mercaptopropionate), trimethylolpropane tri(3-mercaptopropionate) or glycol di-(3-mercaptopropionate), or products of esterification of polyoxyalkylenediols or -triols, of ethoxylated trimethylolpropane or of polyester diols with thiocarboxylic acids such as thioglycolic acid or 2- or 3-mercaptopropionic acid; or
further compounds containing mercapto groups, such as, in particular, 2,4,6-trimercapto-1,3,5-triazine, 2,2'-(ethylenedioxy)diethanethiol (triethylene glycol dimercaptan) or ethanedithiol.

The hardener component preferably contains a low level of toxic phenol compounds which cannot be incorporated chemically into the epoxy polymer, more particularly those compounds selected from the group consisting of phenol, cresol, resorcinol, tert-butylphenol, nonylphenol and dodecylphenol. It contains preferably less than 5 weight %, more preferably less than 1 weight %, more particularly less than 0.1 weight %, of such phenol compounds. With greatest preference the hardener component is entirely free from such phenol compounds. From a toxicological standpoint, an epoxy resin composition of this kind is particularly advantageous.

The hardener component further preferably comprises a low level of amines having a molecular weight of less than 120 g/mol. It contains preferably less than 2 weight %, especially less than 1 weight %, of amines having a molecular weight of below 120 g/mol. An epoxy resin composition of this kind is particularly advantageous from the standpoints of toxicology and odor.

The amount of the reaction product described in the epoxy resin composition is preferably such that 30% to 100%, preferably 50% to 100%, more particularly 70% to 100%, of the entire amine hydrogens in the hardener component originate from the reaction product.

The epoxy resin composition optionally comprises further constituents, particularly auxiliaries and adjuvants customarily used in epoxy resin compositions, examples being the following:
solvents, diluents, or extenders, such as especially the aforementioned diluents;
reactive diluents, especially reactive diluents containing epoxide groups, as mentioned above, epoxidized natural oils like soybean oil, linseed oil or palm kernel oil, or compounds containing acetoacetate groups, especially acetoacetylated polyols, butyrolactone, carbonates, aldehydes, and also, moreover, isocyanates or silicones containing reactive groups;
polymers, especially polyamides, polysulfides, polyvinylformal (PVF), polyvinylbutyral (PVB), polyurethanes (PU), polymers with carboxyl groups, polyamides, butadiene-acrylonitrile copolymers, styrene-acrylonitrile copolymers, butadiene-styrene copolymers, homo- or copolymers of unsaturated monomers, especially from the group encompassing ethylene, propylene, butylene, isobutylene, isoprene, vinyl acetate or alkyl (meth)acrylates, especially chlorosulfonated polyethylenes or fluorine-containing polymers, sulfonamide-modified melamines or purified montan waxes;
inorganic or organic fillers, especially ground or precipitated calcium carbonates, with or without a coating of fatty acids, more particularly of stearates, baryte (heavy spar), talcs, finely ground quartzes, silica sand, iron mica, dolomites, wollastonites, kaolins, mica (potassium aluminum silicate), molecular sieves, aluminum oxides, aluminum hydroxides, magnesium hydroxide, silicas, cements, gypsums, fly ashes, carbon black, graphite, metal powders such as aluminum, copper, iron, zinc, silver or steel, PVC powders or hollow beads;
fibers, especially glass fibers, carbon fibers, metal fibers, ceramic fibers, or polymeric fibers such as polyamide fibers or polyethylene fibers;
pigments, especially titanium dioxide and/or iron oxides;
the aforementioned accelerators;
rheology modifiers, especially thickeners or antisettling agents;
adhesion promoters, especially organoalkoxysilanes;
stabilizers against oxidation, heat, light or UV radiation;
flame retardants, especially aluminum hydroxide (ATH), magnesium dihydroxide (MDH), antimony trioxide, antimony pentoxide, boric acid ($B(OH)_3$), zinc borate, zinc phosphate, melamine borate, melamine cyanurate, ammonium polyphosphate, melamine phosphate, melamine pyrophosphate, polybrominated diphenyl oxides or diphenyl ethers, phosphates such as especially diphenyl cresyl phosphate, resorcinol bis(diphenyl phosphate), resorcinol diphosphate oligomer, tetraphenyl-resorcinol diphosphite, ethylenediamine diphosphate or bisphenol A bis(diphenyl phosphate), tris(chloroethyl) phosphate, tris(chloropropyl) phosphate or tris(dichloroisopropyl) phosphate, tris[3-bromo-2,2-bis(bromo-methyl)propyl] phosphate, tetrabromobisphenol A, bis(2,3-dibromopropyl ether) of bisphenol A, brominated epoxy resins, ethylenebis(tetrabromo-phthalimide), ethylenebis(dibromonorbornanedicarboximide), 1,2-bis(tribro-mophenoxy)ethane, tris(2,3-dibromopropyl) isocyanurate, tribromophenol, hexabromocyclododecane, bis(hexachlorocyclopentadieno)cyclooctane or chlorinated paraffins;

surface-active substances, especially wetting agents, flow control agents, deaerating agents or defoamers;

biocides, such as, for example, algicides, fungicides or fungal growth inhibitors.

If used as an adhesive, the epoxy resin composition preferably comprises fillers and/or pigments and/or accelerators.

The ratio of the number of groups that are reactive toward epoxide groups in the epoxy resin composition, to the number of epoxide groups, is preferably in the range from 0.5 to 1.5, more particularly 0.8 to 1.2.

The components of the epoxy resin composition are each stored in their own container. Further constituents of the epoxy resin composition may be present as part of the resin component or of the hardener component, with further constituents that are reactive toward epoxide groups preferably being part of the hardener component. A suitable container for storing the resin component or the hardener component is, in particular, a drum, a hobbock, a pouch, a pail, a canister, a cartridge, a tube or a bottle. The components are storable, meaning that they can be kept for several months up to a year or more before being employed, without suffering alteration in their respective properties to any extent relevant for their use. For the use of the epoxy resin composition, the resin component and the hardener component are mixed with one another shortly before or during application. The mixing ratio between the components is preferably selected such that the groups of the hardener component that are reactive toward epoxide groups are present in an appropriate ratio to the epoxide groups of the resin component, as described above. In terms of parts by weight, the mixing ratio between the resin component and the hardener component is customarily in the range from 1:10 to 10:1.

The components are mixed by means of a suitable method. Mixing may take place continuously or batchwise. If mixing takes place prior to application, it should be ensured that not too much time elapses between the mixing of the components and application, since otherwise there may be disruptions, such as retarded or incomplete development of adhesion, for example. Mixing takes place in particular at ambient temperature, which is typically in the range from about 5 to 50° C., preferably at about 10 to 30° C.

The mixing of the components is at the same time the start of curing through chemical reaction. In this reaction, the epoxide groups react with the amino groups bearing amine hydrogen, and optionally with further groups present that are reactive toward epoxide groups, in a ring-opening reaction leading to amino alcohol units. Further epoxide groups react with themselves in an anionic polymerization. As the result of these reactions, the composition cures to form a cross-linked material. The person skilled in the art is aware that primary amino groups are difunctional with respect to epoxide groups, and that one primary amino group therefore counts as two groups reactive toward epoxide groups. Curing takes place in particular at ambient temperature. It typically extends over several hours to days, until it has largely concluded under the prevailing conditions. Important influencing factors here include the temperature, the stoichiometry, and the presence of accelerators.

A cured primer or adhesive is obtained from the curing of the epoxy resin composition.

The epoxy resin composition is applied to at least one substrate, those below being particularly suitable:
glass, glass-ceramic, concrete, mortar, cement screed, anhydrite screed, magnesia screed, brick, tile, plaster or natural stones such as granite or marble;
metals or alloys such as aluminum, iron, steel or nonferrous metals, or surface-enhanced metals or alloys such as galvanized or chromed metals;
wood, woodbase materials bonded with resins, such as phenolic, melamine or epoxy resins, or other polymer composites;
plastics, especially rigid or flexible PVC, ABS, polycarbonate (PC), polyamide (PA), polyesters, PMMA, epoxy resins, PU, POM, PO, PE, PP, EPM or EPDM, the plastics having optionally been surface-treated by plasma, corona or flame treatment;
fiber-reinforced plastics, such as carbon fiber-reinforced plastics (CRP), glass fiber-reinforced plastics (GRP) or sheet molding compounds (SMC);
coated substrates, such as powder-coated metals or alloys; paints or varnishes.

As and when necessary, the substrates may be pretreated before the epoxy resin composition is applied. Such pretreatments include, in particular, physical and/or chemical cleaning techniques, as for example sanding, sandblasting, shotblasting, brushing and/or blowing, and also, furthermore, treatment with cleaners or solvents, or the application of an adhesion promoter, an adhesion promoter solution or a primer.

Porous mineral substrates are preferably pretreated so as to present an open-pored, largely dust-free surface without a cement skin.

A further subject of the invention is a primer comprising
a resin component comprising at least one epoxy resin, as described above, and
a hardener component comprising at least one reaction product from the reaction of at least one amine of formula (I) with at least one carbonyl compound of the formula (II) and hydrogen, as described above.

The primer more particularly has a viscosity at 20° C. of not more than 5 Pa·s. The viscosity at 20° C. is preferably in the range from 0.3 to 4 Pa·s, more particularly 0.5 to 3 Pa·s.

The viscosity is determined by thoroughly mixing the components of the primer, by stirring or shaking, and measuring the viscosity 5 minutes after mixing, at a shear rate of $10\ s^{-1}$, on a cone/plate viscometer thermostated to 20° C., with a cone diameter of 50 mm, a cone angle of 1°, and a distance of 0.05 mm between cone tip and plate.

The primer is thereby especially suitable for the pretreatment of porous mineral substrates, being of sufficiently low viscosity to penetrate a porous mineral substrate to which it is applied, at ambient temperatures, effectively enough that the pores of the substrate are filled with primer and closed.

Further to the reaction product described, the primer preferably comprises a diluting substance, more particularly a diluent or a further amine.

An especially suitable further amine is $N^1$-benzyl-1,2-propanediamine or $N^2$-benzyl-1,2-propanediamine or any desired mixtures of the isomers, N-benzyl-1,3-bis(aminomethyl)benzene, N-benzyl-1,3-bis(aminomethyl)cyclohexane, TMD, $H_{12}$-MDA, IPDA, 2- or 4-methyl-1,3-diaminocyclohexane or mixtures thereof, 1,3-bis(aminomethyl)cyclohexane, 1,4-bis(aminomethyl)cyclohexane, NBDA, MXDA, BHMT, TETA, TEPA, PEHA, DPTA, N4-amine, DMAPA or DMAPAPA.

The primer preferably comprises at least one diluent selected from the group consisting of benzyl alcohol, styrenized phenol, ethoxylated phenol, aromatic hydrocarbon resins containing phenol groups, and cardanol.

The primer contains preferably 1.5 to 30 weight %, more particularly 3 to 20 weight %, of such a diluent.

The diluent is preferably at least partially a constituent of the hardener component.

The hardener component contains preferably 5 to 60 weight %, more particularly 10 to 50 weight %, of diluent.

A particularly preferred diluent is benzyl alcohol. Benzyl alcohol has a particularly high diluting effect and is especially compatible with the epoxide polymer.

Another particularly preferred diluent is cardanol. It produces particularly rapid curing. Cardanol is a renewable raw material and represents a phenol compound of particularly low toxicity. It is obtained from cashew shell oil and comprises as principal constituents 3-(pentadeca-8-enyl)phenol, 3-(pentadeca-8,11-dienyl)phenol and 3-(pentadeca-8,11,14-trienyl)phenol).

The hardener component of the primer preferably contains less than 0.1 weight % of phenol compounds selected from the group consisting of phenol, cresol, resorcinol, tert-butylphenol, nonylphenol and dodecylphenol. With particular preference the hardener component is completely free from such phenol compounds. A primer of this kind is particularly advantageous from a toxicological standpoint.

Primers are often applied over large areas—for example, as a priming coat for liquid-applied floor coatings. In this case, a requirement is for very rapid curing even at cold ambient temperatures, so that the primer is amenable to foot traffic as soon as possible, for the subsequent operations. In order to be amenable to foot traffic, the primer must not only have undergone slight initial curing, but must have a non-tacky, load-bearing surface. Furthermore, in the case of large-area application, the worker and the environment are particularly subject to the chemically unincorporable substances contained within the primer. As a result, the cure rate requirements and the difficulties with toxic phenol compounds are particularly high in primer applications.

In one preferred embodiment, the primer is applied and/or cured at a temperature below 20° C.

More particularly it can be applied and/or cured at below 15° C. or 10° C., being of sufficiently low viscosity for the pretreatment of porous mineral substrates, and curing rapidly and without defects.

After the components have been mixed, the primer has a fluid consistency with good leveling qualities. For application, the freshly mixed primer, which is still liquid, is applied within its open time to a flat or slightly inclined surface, typically by being applied by coarse brush, fine brush, roller or doctor blade in such a way that the base or the substrate is wetted thoroughly and covered uniformly.

The "open time" or else "pot life" here is the interval between the mixing of the components and the moment at which the primer can no longer be properly applied. A typical measure of the end of the pot life is the attainment of a defined viscosity level.

Likewise possible is the application of the mixed primer to the substrate by spraying or squirting, using suitable apparatus. This may be done by means of air or using airless spraying equipment.

In the case of a porous substrate, the primer is typically applied in a quantity such that, after curing, the primer forms an impervious film on the surface and, in so doing, seals the pores. In the case of particularly porous substrates, it may be advantageous to apply the primer in two passes, in order to obtain a pore-free, impervious surface.

In the case of a nonporous substrate, the primer is applied typically in a layer thickness in the range from 0.1 to 0.5 mm.

If desired, the primer, before being processed, may be admixed with filler or fibers or other so-called standardizers, so that it has a thickened, slightly thixotropic consistency and runs to less of an extent when applied to inclined surfaces or overhead.

The porous mineral substrate is, in particular, a substrate based on cement, anhydrite (calcium sulfate) or magnesia (magnesite), such as, in particular, concrete, mortar, cement screed, anhydrite screed or magnesia screed, or brick, tile, plaster or natural stone.

A preferred substrate is one based on cement, anhydrite or magnesia. These substrates typically constitute the base for liquid-applied floor coatings in buildings, where the difficulty is that the curing of the floor coating may be disrupted by moisture within the substrate, and unattractive craters and blisters on the surface of the cured coating may occur as a result of pores in the substrate. The use of the primer of the invention as a priming coat on these substrates closes the pores, seals the substrate, and acts as a tie coat and barrier to moisture from below, thereby readying the substrate ideally for overcoating with a curable polymer composition.

The primer may also be used as a priming coat for metals, plastics or wood, more particularly for iron, steel or coatings of plastic, in which case iron and steel may be in galvanized, chrome-plated or coated form or in the form of an alloy.

A further subject of the invention is a layer structure comprising
  at least one layer of the primer of the invention, particularly in an amount such that the primer, after curing, forms an impervious film and closes pores which are present,
  at least one layer of a curable polymer composition,
  optionally a top layer and/or seal coat.

The layer structure preferably constitutes a coating system, in which case the curable polymer composition is a polymeric coating and is present in particular in a layer thickness in the range from 0.5 to 3 mm.

The polymeric coating in this case is more particularly
  a one-component or a two- or multi-component polyurethane or polyurea coating,
  a two- or multi-component epoxy resin coating,
  a one-component or two- or multi-component coating based on a polymer containing silane groups, and optionally further comprising an epoxy resin,
  an aqueous coating based on at least one polymeric dispersion comprising polymers based on polyurethane, acrylate, styrene-butadiene, PVA or copolymers thereof,
  a two- or multi-component aqueous epoxy resin coating comprising a water-thinnable hardener and an epoxy resin emulsion, or
  a two- or multi-component aqueous polyurethane coating comprising a polyol emulsion and an emulsifiable isocyanate component.

The polymeric coating here may be applied in one or more layers. Typically it is applied in one layer or, in particular, in two layers.

Likewise possible is a layer structure consisting of a plurality of layers of different polymeric coatings.

A "seal coat" is a transparent of pigmented, high-grade coating which is applied as an uppermost, thin layer to a coating. It protects and enhances the surface of said coating and closes pores which are still present. The layer thickness of a seal coat (in the dry state) is typically in the range from 0.03 to 0.3 mm.

The coating system is used preferably as a floor covering or floor coating for interiors such as offices, industrial halls, sports halls or cooling rooms, or, in the exterior segment, for balconies, terraces, parking decks, bridges, roofs, sports pitches or playgrounds, as a protective coating for concrete, cement, metals, plastics or wood, as for example for the surface sealing of wooden constructions, vehicles, loading areas, tanks, silos, shafts, machines or steel constructions, as for example of ships, piers, offshore platforms, sluice gates, hydroelectric power stations, river constructions, swimming pools, wind turbines, bridges, chimneys, cranes or sheet-pile walls, or as a sealant, especially for the sealing of bridges or roofs.

When used as a bridge sealant, the coating system may additionally be overcoated with a further suitable covering, more particularly cast asphalt or concrete.

When used as a roof sealant, the coating system may additionally be overcoated with gravel and/or earth.

With particular preference the coating system represents a floor or a protective coating or a water sealant.

The layer structure may also constitute an adhesive bond, in which case the curable polymer composition is an adhesive and there is an outer layer in the form of a bonded substrate.

One example of a layer structure of this kind is a bonded wooden floor, in which case, for example, a cement screed is primed with the primer of the invention, and wooden flooring elements are adhered directly onto the pretreated cement screed by means of an adhesive, as for example an elastic polyurethane adhesive.

A further subject of the invention is a method for coating or bonding a porous mineral substrate, comprising the steps of
(i) applying the above-described primer to the porous mineral substrate, more particularly in an amount sufficient to close the pores,
(ii) curing the applied primer at ambient temperature, in particular at least to capacity to accept foot traffic,
(iii) applying at least one layer of a curable polymer composition to the applied and at least partly cured primer.

The primer here is applied and/or cured in particular at a temperature below 20° C.

The method is preferably a method for coating.

In that case the curable polymer composition is more particularly a polymeric coating and is applied in particular in a layer thickness in the range from 0.5 to 3 mm.

In one embodiment the epoxy resin composition is used as an adhesive. Adhesives based on epoxy resins are employed typically for applications requiring high adhesive force, strength and/or stiffness and weathering stability, in the form, for example, of a bodywork adhesive, sandwich element adhesive, bridge element adhesive or anchoring adhesive. Depending on application, the adhesive is to be workable at ambient temperature and to be load-bearing at an early stage, and therefore is to develop strength rapidly, in particular even without being additionally heated.

A further subject of the invention is therefore an adhesive comprising
 a resin component comprising at least one epoxy resin, as described above, and
 a hardener component comprising at least one reaction product from the reaction of at least one amine of formula (I) with at least one carbonyl compound of the formula (II) and hydrogen, as described above.

The adhesive preferably further comprises at least one further constituent selected from fillers, accelerators and further amines, as have already been stated.

Suitability as filler is possessed in particular by ground or precipitated calcium carbonates, which are optionally coated with fatty acids, especially stearates, and by finely ground quartz, silica sand, kaolins, silicas, cements, gypsums or fly ashes.

An especially suitable accelerator is salicylic acid or 2,4,6-tris(dimethyl-aminomethyl)phenol or a combination thereof.

Suitability as further amine is possessed in particular by $N^1$-benzyl-1,2-propanediamine or $N^2$-benzyl-1,2-propanediamine or any desired mixtures of these isomers, N-benzyl-1,3-bis(aminomethyl)benzene, N-benzyl-1,3-bis(aminomethyl)cyclohexane, IPDA, MXDA, BHMT, TETA, TEPA, PEHA, DPTA, N4-amine, DMAPA or DMAPAPA.

As an adhesive, the composition, after the two components have been mixed, typically has a viscous to pasty consistency. On application, the freshly mixed adhesive is applied within its open time to at least one of the substrates to be bonded, and the two substrates are joined to form an adhesive bond within the open time of the adhesive.

The "open time" here is the interval between the mixing of the components and the point in time at which sufficient deformability of the adhesive and/or sufficient adhesion to the substrates is no longer ensured.

The freshly mixed adhesive is applied in particular by means of a brush, roller, spatula, doctor blade, trowel or from a tube, cartridge or metering apparatus.

The adhesive is particularly suitable for structural bonding in the construction or manufacturing industry, more particularly as an adhesive mortar, assembly adhesive, anchoring adhesive (anchor adhesive), reinforcing adhesive, such as, in particular, for the bonding of strips of CRP or steel to concrete, masonry or wood, as an element adhesive for, for example, bridges, a sandwich element adhesive, facade element adhesive, reinforcing adhesive, bodywork adhesive or half-shell adhesive for rotor blades.

The adhesive is likewise suitable for the filling of cavities such as cracks, gaps or drill holes, in which case the adhesive is filled or injected into the cavity and, after curing, fills up this cavity and bonds or joins the sides of the cavity to one another in a force-fitting manner.

In one embodiment, the adhesive comprises at least one filler, more particularly at least one finely ground quartz or at least one silica sand. An adhesive of this kind is inexpensive and of particularly high compressive strength. It is especially suitable for applications in the construction sector, as a so-called adhesive mortar, for instance.

The result of using the adhesive is a bonded article. The article is more particularly a house, a bathroom, a kitchen, a staircase, a roof, a balcony, a terrace, a parking deck, a bridge, a tunnel, a sandwich element or lightweight construction, a solar panel such as photovoltaic modules or solar heating modules, a facade, a household appliance, a rotor blade of a wind turbine, an automobile, a bus, a truck, a rail vehicle, a ship, an aircraft, a helicopter, or a component for installation in or on such an article.

The adhesive is used more particularly in a method for adhesive bonding, comprising the steps of
mixing the resin component and the hardener component by a suitable technique, and
either
applying the mixed adhesive to at least one of the substrate surfaces to be bonded,
joining the substrates to form a bond within the open time of the adhesive,
or
applying the mixed adhesive into a cavity or gap between two substrates,
optionally inserting an anchor into the cavity or gap within the open time of the adhesive,
followed by the curing of the adhesive.

The "anchor" in this context refers more particularly to a ferrous reinforcing element, a threaded steel element or a bolt. One such is bonded or anchored in an inside or outside wall, ceiling or floor in such a way that a part thereof is force-fittingly bonded and a part thereof protrudes and can be subjected to load.

The adhesive is preferably applied and cured at ambient temperature, more particularly at a temperature in the range from 5 to 35° C., especially 10 to 30° C. This allows the adhesive to be handled particularly easily, and is advantageous in particular outdoors, on building sites and in unheated industrial halls.

A further subject of the invention is a reaction product from the reaction of at least one amine of the formula (I) with at least one carbonyl compound of the formula (II) and hydrogen, the amine and the carbonyl compound, in a molar ratio in the range from 1/0.8 to 1/1.1, being subjected to catalytic hydrogenation with molecular hydrogen in a solvent, without isolation of the imine intermediate formed and without removal of the water liberated.

Hydrogenation takes place preferably under a hydrogen pressure of 5 to 100 bar, at a temperature of 40 to 120° C., more particularly 60 to 100° C., and in the presence of a suitable catalyst. Preferred as catalyst are palladium on carbon (Pd/C), platinum on carbon (Pt/C), Adams catalyst or Raney nickel, more particularly palladium on carbon.

The amine and the carbonyl compound are preferably used in a molar ratio in the range from 1/0.9 to 1/1.

A preferred solvent is an alcohol or an ester or a mixture of alcohol and ester. Particularly preferred is ethanol or isopropanol or ethyl acetate or a combination thereof. Especially suitable is isopropanol or a mixture of isopropanol and ethyl acetate.

After the hydrogenation, the solvent is preferably removed by distillation, especially together with the water liberated.

A reaction product prepared in this way is of particularly low viscosity and high reactivity and is therefore especially suitable for use in a primer based on epoxy resin that is suitable for the pretreatment of porous mineral substrates.

Because the imine intermediate formed is not isolated before the hydrogenation, and the water liberated is not removed, the reaction product includes a particularly large amount of amine of the formula (III) and a particularly small amount of polyalkylated products, this being extremely advantageous with regard to its diluent effect on the epoxy resin and its reactivity with the epoxy resin.

EXAMPLES

Set out below are working examples which are intended to elucidate in more detail the invention described. The invention is of course not confined to these working examples described.

"AHEW" stands for the amine hydrogen equivalent weight.
"EEW" stands for the epoxide equivalent weight.
"Standard conditions" refer to a temperature of 23±1° C. and a relative atmospheric humidity of 50±5%. "SC" stands for "standard conditions".
Description of Measurement Methods:
Infrared spectra (FT-IR) were measured as undiluted films on an FT-IR instrument 1600 from Perkin-Elmer equipped with a horizontal ATR measurement unit with ZnSe crystal; the absorption bands are reported in wavenumbers ($cm^{-1}$); (measuring window: 4000-650 $cm^{-1}$).

The viscosity was measured on a thermostated cone/plate viscometer, Rheotec RC30 (cone diameter 50 mm, cone angle 1°, cone tip/plate distance 0.05 mm) at a shear rate of 10 $s^{-1}$.

The amine number was determined by titration (with 0.1N $HClO_4$ in acetic acid against crystal violet).
Commercial Substances Used:
Araldite® GY 250: bisphenol A diglycidyl ether, EEW about 187.5 g/eq (from Huntsman)
Araldite® DY-E: monoglycidyl ether of $C_{12}$ to $C_{14}$ alcohols, EEW about 290 g/eq (from Huntsman)
SR-Dur® 2750: Mannich base based on 4-tert-butylphenol, 1,3-bis(aminomethyl)benzene and trimethyl-1,6-hexanediamine, containing 10 to 25 weight % of 4-tert-butylphenol, AHEW 75.0 g/eq (from SRS Meeder)
Preparation of Inventive Reaction Products:
Reaction Product A1: Reaction Product Comprising N-(2-hydroxybenzyl)-1,3-bis(aminomethyl)benzene A round-bottomed flask was charged at room temperature with 27.24 g (0.20 mol) of 1,3-bis(aminomethyl)benzene (MXDA, from Mitsubishi Gas Chemicals) under a nitrogen atmosphere. With thorough stirring, a solution of 24.42 g (0.20 mol) of salicylaldehyde in 250 ml of isopropanol was added slowly dropwise, followed by stirring for 2 hours. Thereafter the reaction mixture was hydrogenated under a hydrogen pressure of 80 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 $cm^{-1}$ had disappeared. At that point the hydrogenated solution was concentrated under reduced pressure at 65° C. This gave a yellowish liquid having a viscosity of 22.1 Pa·s at 20° C. and an amine number of 458 mg KOH/g.

FT-IR: 3022, 2846, 2721, 2613, 1587, 1454, 1254, 1082, 843, 747, 699.
Reaction Product A2: Reaction Product Comprising N-(2-hydroxybenzyl)-1,3-bis(aminomethyl)cyclohexane A round-bottomed flask was charged at room temperature with 14.22 g (0.10 mol) of 1,3-bis(aminomethyl)cyclohexane (1,3-BAC, from Mitsubishi Gas Chemicals) under a nitrogen atmosphere. With thorough stirring, a solution of 12.21 g (0.10 mol) of salicylaldehyde in 350 ml of isopropanol was added slowly dropwise, followed by stirring for 2 hours. Thereafter the reaction mixture was hydrogenated under a hydrogen pressure of 90 bar, at a temperature of 90° C. and with a flow rate of 4 ml/min, on a continuous hydrogenation apparatus with Pd/C fixed-bed catalyst. To monitor the reaction, IR spectroscopy was used to verify whether the imine band at about 1665 $cm^{-1}$ had disappeared. At that point the hydrogenated solution was concentrated under reduced pressure at 65° C. This gave a yellowish liquid having a viscosity of 124 Pa·s at 20° C. and an amine number of 445 mg KOH/g.

FT-IR: 2915, 2846, 2726, 1589, 1455, 1413, 1257, 1151, 1102, 1036, 953, 931, 842, 793, 720.

Preparation of Noninventive Reaction Products as a Comparison:

Reaction Product R1: Reaction Product Comprising N-(2-hydroxybenzyl)-4-methyl-1,5-pentanediamine A round-bottomed flask was charged at room temperature with 23.24 g (0.20 mol) of 1,5-diamino-2-methylpentane (Dytek® A, from Invista) under a nitrogen atmosphere. With thorough stirring, a solution of 24.42 g (0.20 mol) of salicylaldehyde in 250 ml of isopropanol was added slowly dropwise, followed by stirring for 2 hours. Thereafter the reaction mixture was hydrogenated under a hydrogen pressure of 80 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a yellowish liquid having a viscosity of 2.3 Pa·s at 20° C. and an amine number of 506 mg KOH/g.

Reaction Product R2: Reaction Product Comprising N-(2-hydroxybenzyl)-3,3(5),5-trimethyl-1,6-hexanediamine A round-bottomed flask was charged at room temperature with 15.82 g (0.10 mol) of 2,2(4),4-trimethylhexamethylenediamine (Vestamin® TMD, from Evonik) under a nitrogen atmosphere. With thorough stirring, a solution of 12.21 g (0.10 mol) of salicylaldehyde in 250 ml of isopropanol was added slowly dropwise, followed by stirring for 2 hours. Thereafter the reaction mixture was hydrogenated under a hydrogen pressure of 80 bar, at a temperature of 90° C. and with a flow rate of 4 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a dark yellow liquid having a viscosity of 4.4 Pa·s at 20° C. and an amine number of 414 mg KOH/g.

Reaction Product R3: Reaction Product Comprising N-(2-hydroxybenzyl)-4,7-diaza-1,10-decanediamine A round-bottomed flask was charged at room temperature with 34.85 g (0.20 mol) of N,N'-bis(3-aminopropyl)ethylenediamine (N4-amine, from BASF) under a nitrogen atmosphere. With thorough stirring, a solution of 24.42 g (0.20 mol) of salicylaldehyde in 400 ml of isopropanol was added slowly dropwise, followed by stirring for 2 hours. Thereafter the reaction mixture was hydrogenated under a hydrogen pressure of 85 bar, at a temperature of 90° C. and with a flow rate of 4 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a yellowish liquid having a viscosity of 2.5 Pa·s at 20° C. and an amine number of 794 mg KOH/g.

Reaction Product R4: Reaction Product Comprising N-benzyl-1,3-bis(amino-methyl)benzene A round-bottomed flask was charged at room temperature with 27.24 g (0.20 mol) of 1,3-bis(aminomethyl)benzene (MXDA, from Mitsubishi Gas Chemicals) under a nitrogen atmosphere. With thorough stirring, a solution of 26.53 g (0.25 mol) of benzaldehyde in 250 ml of isopropanol was added slowly dropwise, followed by stirring for 2 hours. Thereafter the reaction mixture was hydrogenated under a hydrogen pressure of 80 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a yellowish liquid having a viscosity of 0.1 Pa·s at 20° C. and an amine number of 438 mg KOH/g.

Reaction Product R5: Reaction Product Comprising N-(4-hydroxybenzyl)-1,3-bis(aminomethyl)benzene A round-bottomed flask was charged at room temperature with 27.24 g (0.20 mol) of 1,3-bis(aminomethyl)benzene (MXDA, from Mitsubishi Gas Chemicals) under a nitrogen atmosphere. With thorough stirring, a solution of 24.42 g (0.20 mol) of 4-hydroxybenzaldehyde in 250 ml of isopropanol was added slowly dropwise, followed by stirring for 2 hours. Thereafter the reaction mixture was hydrogenated under a hydrogen pressure of 80 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a highly viscous yellowish liquid having a viscosity of >200 Pa·s at 20° C. and 8 Pa·s at 60° C.

Reaction Product R6: Reaction Product Comprising N-(4-hydroxy-2-methoxy-benzyl)-1,3-bis(aminomethyl)benzene A round-bottomed flask was charged at room temperature with 27.24 g (0.20 mol) of 1,3-bis(aminomethyl)benzene (MXDA, from Mitsubishi Gas Chemicals) under a nitrogen atmosphere. With thorough stirring, a solution of 30.43 g (0.20 mol) of vanillin in 250 ml of isopropanol was added slowly dropwise, followed by stirring for 2 hours. Thereafter the reaction mixture was hydrogenated under a hydrogen pressure of 80 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a highly viscous orange-colored liquid having a viscosity of >200 Pa·s at 20° C. and 15 Pa·s at 60° C.

Reaction Product R7: N,N'-bis(2-hydroxybenzyl)-1,3-bis(aminomethyl)-benzene

In a round-bottomed flask, 13.62 g (0.10 mol) of 1,3-bis(aminomethyl)benzene (MXDA, from Mitsubishi Gas Chemicals), 24.42 g (0.20 mol) of salicylaldehyde and 400 ml of isopropanol were mixed under a nitrogen atmosphere and stirred at room temperature for 2 hours. Thereafter the reaction mixture was hydrogenated under a hydrogen pressure of 85 bar, at a temperature of 90° C. and with a flow rate of 4 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a highly viscous yellowish liquid having a viscosity of >200 Pa·s at 20° C. and 2.9 Pa·s at 60° C. and an amine number of 303 mg KOH/g.

Production of Epoxy Resin Compositions:

Examples 1 to 7

For each example, the ingredients specified in table 1 were mixed in the stated quantities (in parts by weight) of the resin component using a centrifugal mixer (SpeedMixer™ DAC 150, FlackTek Inc.) and the mixtures were stored in the absence of moisture.

The reaction product specified in table 1, in the stated quantity, was subsequently mixed with the resin component using the centrifugal mixer, processed to a homogeneous liquid, and immediately used and tested as follows:

5 minutes after mixing, the viscosity at 20° C. was ascertained ("Viscosity (5')"). A first film was drawn down in a film thickness of 500 μm onto a glass plate, which was stored and cured under standard conditions. This film was used for determination of the König hardness (pendulum hardness according to König, as per DIN EN ISO 1522, "König hardness (SC)") after 1 day (1 d), 2 days (2 d), 4 days (4 d) and 7 days (7 d). Furthermore, the appearance of the cured film was assessed (denoted "appearance (SC)" in table 1). A film identified as "attractive" there was clear and had a glossy and non-tacky surface without structure. "Structure" here refers to any kind of marking or pattern on the surface.

A second film was drawn down onto a glass plate in a film thickness of 500 μm, and this film, immediately after application, was stored and cured for 7 days at 8° C. and 80% relative humidity and subsequently under standard conditions. Here, again, a determination was made of the König hardness, in each case after 1 day (1 d 8°/80%), 2 days (2 d 8°/80%), 7 days (7 d 8°/80%) and 8 days (+1 d SC). The appearance of this film was then assessed (denoted in table 1 by "appearance (8°/80%)"), in the same way as described for the appearance (SC).

The measure used for the yellowing, moreover, was the color change after exposure in a weathering tester. For this purpose, a further film was drawn down in a film thickness of 500 μm onto a glass plate and was stored, or cured, under standard conditions for 2 weeks and subsequently exposed in a Q-Sun Xenon Xe-1 weathering tester with Q-SUN Daylight-Q optical filter and with a xenon lamp, with a luminous intensity of 0.51 W/m² at 340 nm and at a temperature of 65° C. for 72 hours (Q-Sun (72 h)). There-after the color difference ΔE of the film thus exposed was determined in comparison to the corresponding unexposed film, using an NH310 colorimeter from Shenzen 3NH Technology Co. LTD, equipped with Silicon Photoelectric Diode Detector, Light Source A, Color Space Measurement Interface CIE L*a*b*C*H*. A high ΔE value here represents a large color difference, and severe yellowing.

The results are reported in table 1.

These epoxy resin compositions are suitable as primers or adhesives. The viscosity after the two components have been mixed is a measure of the workability as a primer. The development of the König hardness is a measure of the cure rate and of the ultimate hardness under the respective conditions.

The examples labeled with "(Ref.)" are comparative examples.

TABLE 1

Composition and properties of examples 1 to 7.

| | | 1 | 2 | 3 (Ref.) | 4 (Ref.) | 5 (Ref.) | 6 (Ref.) | 7 (Ref.) |
|---|---|---|---|---|---|---|---|---|
| Resin comp.: | | | | | | | | |
| Araldite ® GY-250 | | 167.2 | 167.2 | 167.2 | 167.2 | 167.2 | 167.2 | 167.2 |
| Araldite ® DY-E | | 31.8 | 31.8 | 31.8 | 31.8 | 31.8 | 31.8 | 31.8 |
| Hardener comp.: | | | | | | | | |
| Reaction product | | A1 | A2 | — | R1 | R2 | R3 | R4 |
| | | 81.0 | 82.8 | | 74.1 | 88.1 | 56.1 | 95.0 |
| SR-Dur ® 2750 | | — | — | 75.0 | — | — | — | — |
| Viscosity | (5') [Pa · s] | 3.5 | 5.1 | 3.3 | 1.7 | 2.4 | 2.6 | 0.51 |
| König | (1 d SC) | 165 | 171 | 168 | 60 | 31 | 74 | 56 |
| hardness | (2 d SC) | 197 | 198 | 182 | 108 | 71 | 87 | 140 |
| [s] | (4 d SC) | 202 | 204 | 203 | 138 | 110 | 87 | 183 |
| | (7 d SC) | 207 | 210 | 205 | 155 | 153 | 95 | 204 |
| Appearance | (SC) | slightly matt | attractive | attractive | slight structure | attractive | tacky, matt | slightly matt |
| Q-Sun | (72 h) ΔE | 5.8 | 5.9 | 23.0 | 12.3 | 5.7 | 6.1 | n.d. |
| König | (1 d 8°/80%) | 14 | 24 | 27 | n.d. | n.d. | n.d. | n.d. |
| hardness | (2 d 8°/80%) | 74 | 83 | 70 | n.d. | n.d. | n.d. | n.d. |
| [s] | (7 d 8°/80%) | 140 | 155 | 120 | 27 | 33 | 52 | 63 |
| | (+1 d SC) | 190 | 182 | 148 | 42 | 84 | 92 | 121 |
| Appearance | (8°/80%) | slightly matt | matt, slight structure | slight structure | matt, slight structure | slightly matt | cloudy, tacky, structure | cloudy, structure |

"n.d." stands for "not determined"

Production of Primers:

Examples 8 to 18

For each example, the ingredients specified in tables 2 to 3 were mixed in the stated quantities (in parts by weight) of the hardener component using a centrifugal mixer (Speed-Mixer™ DAC 150, FlackTek Inc.) and the mixtures were stored in the absence of moisture.

Similarly, the resin component ingredients specified in tables 2 to 3 were processed and stored.

The two components of each primer were subsequently processed at room temperature, using the centrifugal mixer, to give a homogeneous liquid, which was immediately used and tested as follows:

5 minutes after mixing, the viscosity at 20° C. was ascertained ("Viscosity (5')"). Each primer was applied by brush to three concrete garden slabs so that the primer fully covered the surface of the slabs and the pores were closed by the primer. Then one garden slab was stored under standard conditions, and two garden slabs at 8° C. and 80% relative humidity. For determining the time required to regain amenability to accept foot traffic, a determination was then made of the time, under standard conditions (SC) and 8° C. and 80% relative humidity (8°/80%), respectively, that was required until a metal cylinder 24 mm in diameter with a weight of 1 kg, standing on the surface for 60 seconds, no longer experienced sticking and did not leave any mark.

The results are reported in tables 2 to 3.

The examples labeled with "(Ref.)" are not inventive and they serve as a comparison.

Schweiz AG) was applied in a layer thickness of 1.5 mm, by pouring the freshly mixed coating onto the garden slab primed with the respective primer and spreading it using a doctor blade. Alternatively, Sikafloor®-400 N Elastic pebble grey (flexible 1-component polyurethane coating form Sika Schweiz AG) was applied in a layer thickness of 1.5 mm, by pouring it onto the garden slab primed with a respective primer and spreading it using a doctor blade.

After a cure time of 7 days under standard conditions, each garden slab bore a high-quality, multi-coat floor covering with defect-free surface and outstanding adhesion between the coats.

TABLE 2

Composition (in parts by weight) and properties of the primers of examples 8 to 16.

| | Example | | | | | | | | |
|---|---|---|---|---|---|---|---|---|---|
| | 8 | 9 | 10 (Ref.) | 11 (Ref.) | 12 (Ref.) | 13 (Ref.) | 14 (Ref.) | 15 (Ref.) | 16 (Ref.) |
| Resin component: | | | | | | | | | |
| Araldite ® GY-250 | 167.2 | 167.2 | 167.2 | 167.2 | 167.2 | 167.2 | 167.2 | 167.2 | 167.2 |
| Araldite ® DY-E | 31.8 | 31.8 | 31.8 | 31.8 | 31.8 | 31.8 | 31.8 | 31.8 | 31.8 |
| Hardener component: | | | | | | | | | |
| Reaction product | A1 | A2 | — | R1 | R2 | R4 | R5 | R6 | R7 |
| | 81.0 | 82.8 | | 74.1 | 88.1 | 95.0 | 81.0 | 90.8 | 174.0 |
| SR-Dur ® 2750 | — | — | 75.0 | — | — | — | — | — | — |
| Benzyl alcohol | 34.0 | 35.5 | 32.0 | 31.8 | 31.8 | 34.0 | 34.0 | 34.0 | 40.0 |
| Viscosity (5') [Pa · s] | 1.5 | 2.5 | 2.2 | 1.1 | 1.3 | 0.41 | 8.1$^1$ | 12.3$^1$ | 5.1 |
| Amenable to foot traffic | | | | | | | | | |
| under SC | 6.5 h | 6 h | 4.5 h | 8 h | 8 h | 12 h | n.d. | n.d. | 12 h |
| at 8°/80% | 22 h | 20 h | 22 h | 30 h | 48 h | 48 h | n.d. | n.d. | 55 h |

"n.d." stands for "not determined"
$^1$viscosity too high

TABLE 3

Composition (in parts by weight) and properties of the primers of examples 17 and 18.

| | Example | |
|---|---|---|
| | 17 | 18 (Ref.) |
| Resin component: | | |
| Araldite ® GY-250 | 167.2 | 167.2 |
| Araldite ® DY-E | 31.8 | 31.8 |
| Hardener component: | | |
| Reaction product | A1 | — |
| | 81.0 | |
| SR-Dur ® 2750 | — | 75.0 |
| Cardanol$^1$ | 34.6 | 32.0 |
| Viscosity (5') [Pa · s] | 3.8 | 4.9 |
| Amenable to foot traffic | | |
| under SC | 5 h | 4 h |
| at 8°/80% | 18 h | 15 h |

$^1$Cardolite ® NX-2026 from Cardolite Corp.

Production of Coatings:

Examples 19 to 24

The garden slabs of examples 8, 9 and 17, primed with inventive primers, were each coated, after 24 hours of curing at 8° C. and 80% relative humidity, with a commercial floor coating, as specified in table 4. In one case, Sikafloor®-264 pebble grey (2-component epoxy resin coating from Sika

TABLE 4

Structure of the coatings of examples 19 to 24.

| | Example | | | | | |
|---|---|---|---|---|---|---|
| | 19 | 20 | 21 | 22 | 23 | 24 |
| Primer from example | 8 | 8 | 9 | 9 | 17 | 17 |
| Sikafloor ® type | 264 | 400N | 264 | 400N | 264 | 400N |

Production of Adhesives:

Examples 25 and 26

For example 25, the ingredients specified in table 5, in the quantities stated (in parts by weight), of the hardener component were mixed using a centrifugal mixer (Speed-Mixer™ DAC 150, FlackTek Inc.) and stored in the absence of moisture.

For example 26 (comparison), the hardener component used was Sikadur® 31 CF normal component B (from Sika Schweiz AG) in the quantity indicated in table 5.

The resin component used in each case was Sikadur® 31 CF normal component A (from Sika Schweiz AG) with an EEW of about 838 g, in the quantity specified in table 5.

The two components were subsequently processed at room temperature, using the centrifugal mixer, to form a homogeneous paste, which was immediately used and tested as follows:

A number of adhesive bonds were produced, by applying in each case several grams of adhesive to a concrete slab, which had been cleaned with a steel brush, and then adhering to the slab a cylinder of acetone-cleaned steel having a diameter of 20 mm over its base area, the thickness of the bondline being 2 mm. The bonds were stored under standard conditions. After 2 days, they were pulled apart to fracture in a method based on DIN EN 4624 with a testing speed of 2 mm/min, in order to determine the strength of the bond at the maximum force (tensile adhesion, concrete/steel).

Furthermore, a number of bonds were produced by bonding pairs of cylinders made from acetone-cleaned steel, and having a diameter of 20 mm, together at the round base area, using the adhesive, in such a way that the thickness of the bondline was 2 mm. The bonds were stored under standard conditions. After 2 days, they were pulled apart to fracture in a method based on DIN EN ISO 4624 with a testing speed of 2 mm/min, in order to determine the strength of the bond at the maximum force (tensile adhesion, steel/steel).

In addition, the compressive strength was ascertained, by curing and storing the adhesive in the form of blocks with dimensions of 12.7×12.7×25.4 mm under standard conditions. After 2 days and after 7 days, a number of such blocks were compressed according to ASTM D695 at a testing speed of 1.3 mm/min until destruction, with the value of the compressive strength being read off in each case at the maximum force.

The results are reported in table 5.

Example 26, labeled with "(Ref.)", is not inventive and it serves as a comparison.

TABLE 5

Composition (in parts by weight) and properties of the adhesives of examples 25 and 26.

| | | Example | |
| --- | --- | --- | --- |
| | | 25 | 26 (Ref.) |
| Resin component | | | |
| Sikadur ® 31 component A | | 200.0 | 200.0 |
| Hardener component | | | |
| Sikadur ® 31 component B | | — | 100 |
| Reaction product A1 | | 21.0 | — |
| Black iron oxide pigment | | 0.1 | — |
| Finely ground quartz 0-75 μm | | 36.0 | — |
| Silica sand 0.1-0.3 mm | | 27.9 | — |
| Precipitated, stearate-coated chalk | | 15.0 | — |
| Tensile adhesion concrete/steel | 2 days SC | 3.7 MPa[1] | 4.4 MPa[1] |
| Tensile adhesion steel/steel | 2 days SC | 15.2 MPa | 24.5 MPa |
| Compressive strength | 2 days SC | 77.6 MPa | 56.2 MPa |
| | 7 days SC | 86.8 MPa | 64.9 MPa |

[1]Fraction within the concrete

The invention claimed is:

1. An epoxy resin composition comprising at least one reaction product from the reaction of at least one amine of the formula (I) with at least one carbonyl compound of the formula (II) and hydrogen, $$NH_2-CH_2-A-CH_2-NH_2 \quad (I)$$

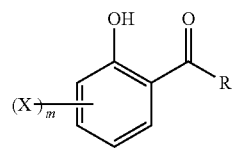
(II)

where
A is a phenylene radical or cyclohexylene radical,
R is a hydrogen radical or alkyl radical having 1 to 8 carbon atoms,
m is 0 or 1, and
X is a hydroxyl radical or methyl radical or methoxy radical,
wherein:
the molar ratio between the amine of the formula (I) and the carbonyl compound of the formula (II) is in the range from 1/0.7 to 1/1.2,
the reaction product contains an amount of amine of the formula (III) in the range from 30 to 80 weight % of the reaction product,

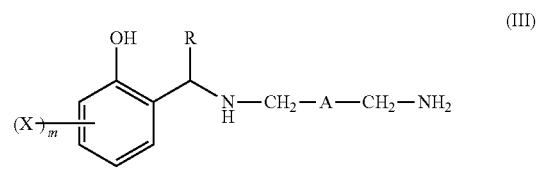

and
the epoxy resin composition is a cold-curing primer or adhesive.

2. The epoxy resin composition as claimed in claim 1, wherein the amine of the formula (I) is selected from the group consisting of 1,3-bis(aminomethyl)benzene and 1,3-bis(aminomethyl)cyclohexane.

3. The epoxy resin composition as claimed in claim 1, wherein the carbonyl compound of the formula (II) is selected from the group consisting of salicylaldehyde and 2'-hydroxyacetophenone.

4. A primer for pretreating porous mineral substrates, comprising:
a resin component comprising at least one epoxy resin and
a hardener component comprising the at least one reaction product as claimed in claim 1.

5. The primer as claimed in claim 4, wherein it has a viscosity at 20° C. of not more than 5 Pa·s, determined as specified in the description.

6. The primer as claimed in claim 4, wherein it comprises at least one diluent selected from the group consisting of benzyl alcohol, styrenized phenol, ethoxylated phenol, aromatic hydrocarbon resins containing phenol groups, and cardanol.

7. The primer as claimed in claim 4, wherein the hardener component comprises less than 0.1 weight % of phenol compounds selected from the group consisting of phenol, cresol, resorcinol, tert-butylphenol, nonylphenol and dodecylphenol.

8. An adhesive comprising
a resin component comprising at least one epoxy resin and
a hardener component comprising the at least one reaction product as claimed in claim 1.

9. A layer structure comprising
at least one layer of the primer as claimed in claim 4,
at least one layer of a curable polymer composition,
optionally an outer layer and/or sealing.

10. The layer structure as claimed in claim 9, wherein it represents a coating system, where the curable polymer composition is a plastics coating.

11. The layer structure as claimed in claim 10, wherein it represents a floor or a protective coating or a water seal.

12. A method for coating or bonding a porous mineral substrate, comprising
   (i) applying the primer as claimed in claim 4 to the porous mineral substrate, in an amount sufficient to close the pores,
   (ii) curing the applied primer at a temperature of 5° C. to 35° C. at least to capacity to accept foot traffic,
   (iii) applying at least one layer of a curable polymer composition to the applied and at least partly cured primer.

13. The method as claimed in claim 12, wherein the primer is applied and/or cured at a temperature of 5° C. to below 20° C.

14. A reaction product containing an amine compound of the formula (III) from the reaction of at least one amine of the formula (I) with at least one carbonyl compound of the formula (II) and hydrogen,

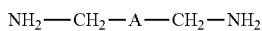
(I)

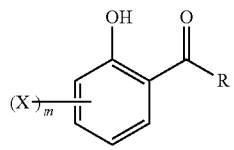
(II)

where

A is a phenylene radical or cyclohexylene radical,

R is a hydrogen radical or alkyl radical having 1 to 8 carbon atoms, m is 0 or 1, and X is a hydroxyl radical or methyl radical or methoxy radical, where the amine and the carbonyl compound in a molar ratio in the range from 1/0.8 to 1/1.1 are subjected to catalytic hydrogenation with molecular hydrogen in a solvent, without isolation of the imine intermediate formed and without removal of the water liberated, and wherein the reaction product contains an amount of amine of the formula (III) in the range from 30 to 80 weight% of the reaction product,

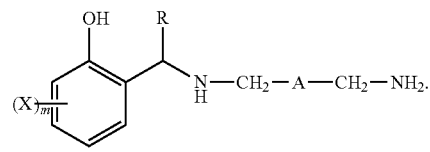
(III)

* * * * *